United States Patent [19]

Belardinelli et al.

[11] Patent Number: 5,446,046
[45] Date of Patent: Aug. 29, 1995

[54] A1 ADENOSINE RECEPTOR AGONISTS AND ANTAGONISTS AS DIURETICS

[75] Inventors: Luiz Belardinelli, Gainesville; Ray Olsson, Tampa; Stephen Baker, Gainesville, all of Fla.; Peter J. Scammells, Highton, Australia

[73] Assignee: University of Florida Research Foundation, Gainesville, Fla.

[21] Appl. No.: 144,459

[22] Filed: Oct. 28, 1993

[51] Int. Cl.$^6$ .............. A61K 31/52; C07D 473/06; C07D 473/08; C07D 519/00
[52] U.S. Cl. .............. 514/263; 544/267; 544/268; 544/271; 544/272; 536/27.62
[58] Field of Search .............. 544/267, 268, 271, 272; 514/263

[56] References Cited

U.S. PATENT DOCUMENTS

| | | | |
|---|---|---|---|
| 3,998,953 | 12/1976 | Konz | 544/267 |
| 4,364,922 | 12/1982 | Berne et al. | 494/9 |
| 4,713,455 | 12/1987 | Furrer | 544/267 |
| 4,980,379 | 12/1990 | Belardinelli et al. | 524/821 |
| 5,288,721 | 2/1994 | Klein | 544/267 |

OTHER PUBLICATIONS

Jacobsen, J Med Chem 35, 407 (1992).
Belardinelli, L. et al. (1989) "The Cardiac Effects of Adenosine" Progress in Cardiovascular Diseases 32:73–97.
Belardinelli, L. et al. (1990) "Cardiac Electrophysiology and Pharmacology of Adenosine" J. Cardiovasc. Electrophysiol. 1:327–339.
Olsson, R. A., J. D. Pearson (1990) "Cardiovascular Purinoceptors" Physiological Reviews 70:761–845.

Primary Examiner—Mark L. Berch
Attorney, Agent, or Firm—Saliwanchik & Saliwanchik

[57] ABSTRACT

Adenosine and xanthine derivatives, and compositions comprising those compounds, are potent selective agonists and antagonists of adenosine receptors. The derivatives and composition are used to treat conditions, including certain cardiac arrhythmias.

3 Claims, 3 Drawing Sheets

A1 ADENOSINE RECEPTOR AGONISTS AND ANTAGONISTS AS DIURETICS

BACKGROUND OF THE INVENTION

Adenosine is an extracellular messenger generated by all cells in the body. Adenosine itself, substances that act as agonists of adenosine, and substances that antagonize its actions have important clinical applications. In the heart, an organ whose function depends critically on an adequate supply of oxygen, adenosine regulates the balance between oxygen supply (coronary blood flow) and oxygen demand (cardiac work). Adenosine released from working heart cells increases oxygen supply through coronary dilation and decreases oxygen consumption by slowing heart rate and modulating $\beta$-adrenergic stimulation. The protective effects of adenosine are particularly important when cardiac oxygen supply is limited, for example, by coronary artery narrowing.

Several recent reviews describe the adenosine system in detail (Belardinelli, L., J. Linden, R. M. Berne [1989] *Prog. Cardiovasc. Dis.* 32:73–97; Belardinelli, L., A. Pelleg [1990] *J. Cardiovasc. Electrophysiol.* 1:327–339; Olsson, R. A., J. D. Pearson [1990] *Physiol. Rev.* 70:761–845). The cardiac adenosine system consists of three processes: (1) mechanisms for adenosine formation; (2) adenosine receptors and proteins that couple them to effectors; and (3) mechanisms for the removal of adenosine. Selective modification of one or more of these systems by means of drugs such as adenosine receptor antagonists and adenosine uptake inhibitors can modify the actions of adenosine for therapeutic benefit.

Adenosine formation increases when oxygen demand exceeds its supply, thereby promoting the degradation of adenosine nucleotides. The degradation of adenylates released from nerve terminals along with neurotransmitters and the degradation of S-adenosylhomocysteine, a byproduct of methylation reactions, are additional sources of adenosine in the heart. Heart muscle and coronary blood vessel cells take up very nearly all the adenosine generated in the heart, reincorporating that adenosine into the cellular nucleotide pool.

At least two types of receptors mediate the actions of adenosine in the heart. $A_1$ adenosine receptors ($A_1AR$) decrease oxygen consumption, for example, by slowing heart rate, and the $A_2$ adenosine receptors ($A_2AR$) increase oxygen supply by causing coronary vasodilation. The actions of adenosine on cardiac cells are either direct (cAMP-independent) or indirect (cAMP-dependent). The direct actions include the negative dromotropic effect on the AV node. Those electrophysiological effects are the basis of adenosine's anti-arrhythmic properties; adenosine is highly effective (>90%) in terminating paroxysmal supraventricular tachycardia (PSVT). Whereas the direct effects of adenosine occur in the absence of agents that act through adenylate cyclase, the indirect effects reflect the inhibition of this enzyme when it is stimulated by agents such as $\beta$-adrenergic agonists.

A number of pharmacological studies employing receptor-selective agonists support the idea that $A_2ARs$ mediate coronary vasodilation. Although endothelial cells contain $A_2ARs$ and thus could play a role in vasodilation, they are not essential, for adenosine acts on coronary smooth muscle cells, causing them to relax.

When adenosine is used as a drug, its side effects are usually mild, a reflection of its extremely rapid degradation in the body (seconds). The safety of adenosine in the diagnosis and treatment of PSVT is now well established. An important factor which has inhibited the therapeutic development of the adenosine analogues is the ubiquitous nature of adenosine's action on a variety of tissues.

Two kinds of drugs modify the actions of adenosine according to whether they magnify or attenuate the effects of the nucleoside. Inhibitors of the cell membrane nucleoside transporter block the removal of adenosine from the extracellular space, thereby increasing its concentration and intensifying its action. Adenosine uptake blockers also inhibit the nucleoside transport system in human erythrocytes and cardiocyte membranes and potentiate the cardiac actions of adenosine in the dog.

Methylxanthines competitively antagonize the binding of adenosine to both the $A_1AR$ and the $A_2AR$. Certain naturally occurring methylxanthines such as caffeine and theophylline antagonize the cardiovascular effects of adenosine. For example, the administration of adenosine to patients receiving theophylline fails to produce AV block or terminate PSVT. However, those methylxanthines are relatively weak and, more importantly, are nonselective, antagonizing both the electrophysiological and vasodilatory effects of adenosine in laboratory animals and humans. Theophylline also ameliorates the non-cardiac effects of adenosine such as flushing, local pain, and respiratory stimulation.

Synthetic alkylxanthines, e.g., 8-cyclopentyl-1,3-dipropylxanthine (CPX; see U.S. Pat. Nos. 4,364,922 and 4,980,379), are significantly more potent and selective antagonists at the $A_1AR$ than are theophylline or caffeine.

BRIEF SUMMARY OF THE INVENTION

The present invention concerns the discovery of certain novel compounds which can bind to adenosine receptors with surprisingly high affinity and selectivity. Specifically exemplified herein are xanthine and adenosine analogues comprising an epoxide moiety. As explained in more detail herein, these adenosine agonists and antagonists have therapeutic utility in a broad range of applications including cardiac and renal regulation. Included among these novel compounds are both adenosine agonists and antagonists.

In one embodiment of the subject invention, the novel compound known as 1,3-dipropyl-8-{3-oxatricyclo[3.1.2.0$^{2,4}$]oct-6(7)-yl}xanthine, herein referred to as ENX, is used as an antagonist of adenosine. Advantageously, ENX has been found to be uniquely potent, specific, and highly selective for the $A_1$ adenosine receptor. The subject invention further concerns other xanthines and adenosines comprising an epoxide moiety in an exocyclic substituent. Further embodiments of the invention include compositions and formulations comprising ENX or those analogues or derivatives which can have therapeutic utility as agonists or antagonists of adenosine.

A further aspect of the subject invention is a method for using the disclosed compounds for modulating the biological activity of adenosine. The compounds, or compositions comprising those compounds, can be utilized for their modulating effect on adenosine, e.g., as agonists or antagonists of the adenosine receptors. The antagonist activity of the subject compounds can be utilized in treating conditions where elevated levels of adenosine are present; the agonists can be useful where stimulation of the adenosine receptor is needed. Such conditions include, but are not limited to, cardiac arrhythmias, renal failure, and maturity onset diabetes.

DETAILED DESCRIPTION OF THE DISCLOSURE

The subject invention pertains to novel compounds, and formulations comprising those compounds, which can advantageously be used as either agonists or antagonists at adenosine receptors. Specifically, these compounds either promote or antagonize the negative dromotropic, chronotropic, and inotropic effects mediated by an $A_1$ adenosine receptor ($A_1AR$).

The subject compounds fall into two general categories: (1) epoxides of xanthine, and (2) epoxides of adenosine. In a preferred embodiment of the subject invention, the xanthine epoxides are 1,3-dialkylxanthines having an epoxide moiety covalently bound to the C-8 substituent. The preferred epoxides of adenosine are those having an epoxide moiety as part of an exocyclic substituent. The general structure of the 1,3-dialkylxanthines is shown below as Structure I:

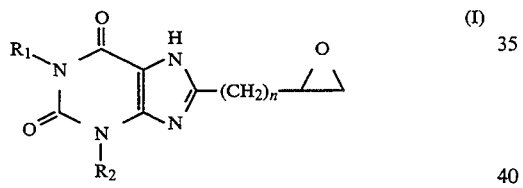
(I)

wherein $R_1$ and $R_2$ are the same or different, and can be an alkyl group of 1-4 carbons in length; and n=0-4.

The general structure of the 1,3-dialkyl-8-epoxybicycloalkylxanthines is shown below as Structure II:

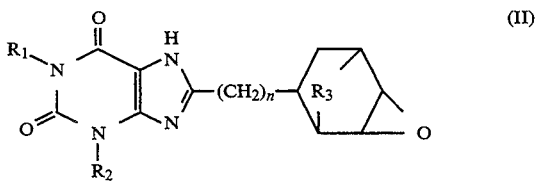
(II)

wherein $R_1$ and $R_2$ are the same or different, and can be an alkyl group of 1-4 carbons; $R_3$ is either O or an alkyl group of 1-4 carbons; and n=0-4.

A polymethylene chain 1-4 carbons in length can link the epoxide moiety to C-8 of 1,3-dialkylxanthine, as in Structure I. Alternatively, the epoxide group can be part of an exocyclic substituent linked to C-8 of the xanthine moiety, either directly or through a (poly)-methylene chain 1-4 carbons long. The exocyclic substituent, as shown in Structure II, can be a bicycloalkyl group, forming an epoxybicycloalkyl substituent. Other exocyclic epoxide structures can also be part of the compound as would be readily recognized by those skilled in the art having the benefit of this disclosure.

The bicycloalkyl group can further comprise an alkenyl group for the formation of a second epoxide moiety.

Figure 1:
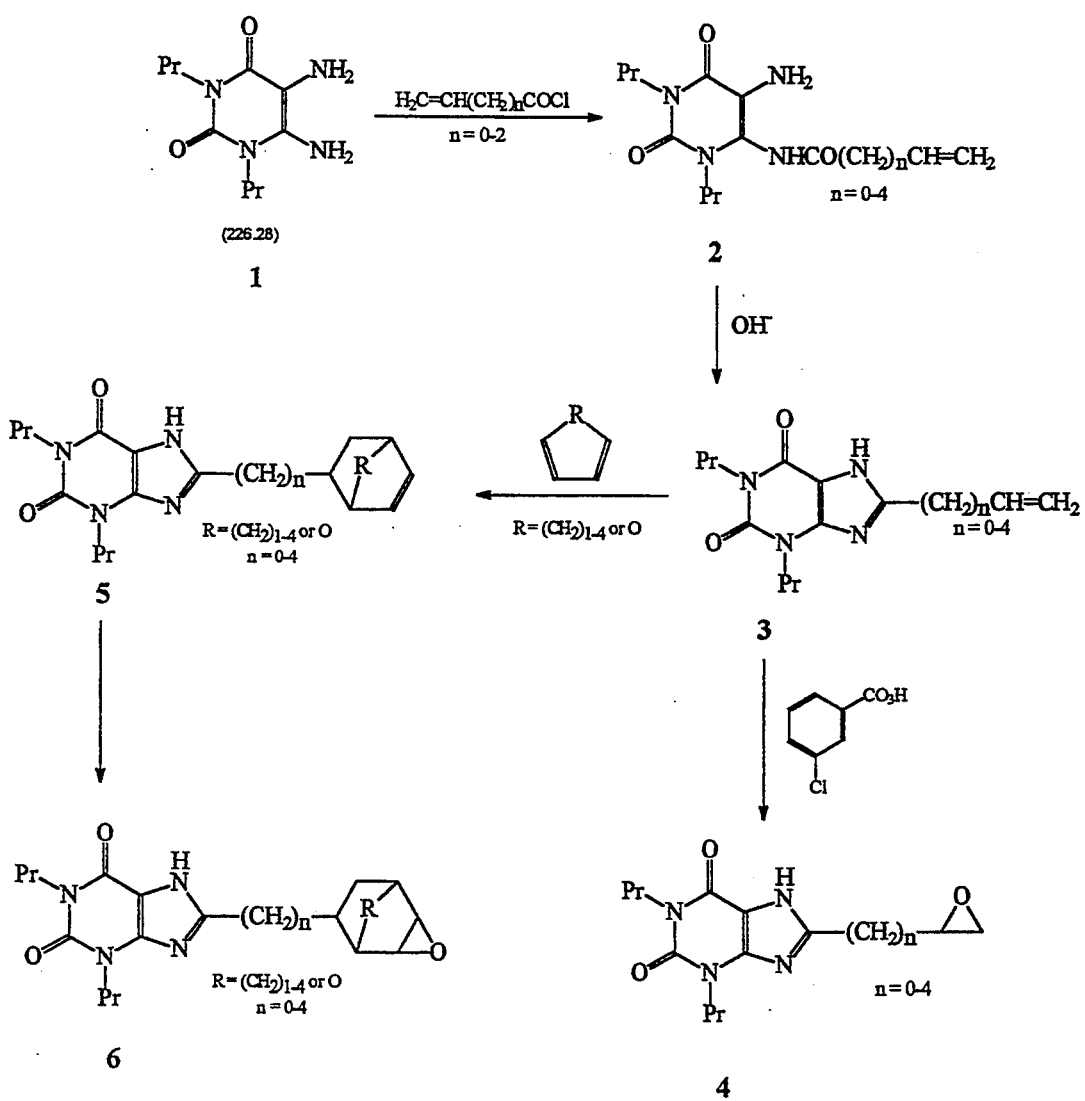
FIG. 1 is a scheme outlining the syntheses of 1,3-dipropylxanthines having C-8 substituents that contain an epoxide moiety.

FIG. 1 depicts the synthesis of 8-substituted 1,3-dipropylxanthine. Derivatives of adenosine containing an epoxide moiety can be used as $A_1AR$ agonists. Epoxide derivatives of adenosine agonists can also display high selectivity for adenosine receptors. High selectivity for cardiac tissue is also demonstrated. More specifically, $N^6$-substitution of adenosine with epoxycycloalkyl groups can result in potent and tissue-selective agonists.

The $N^6$-subregion of the $A_1$ adenosine receptor contains chiral recognition sites which are important for the determination of $A_1/A_2$ selectivity. The epoxide can be substituted as a cycloalkyl substituent, e.g., cyclopropyl, cyclopentyl, norbornyl, or adamantyl derivative of adenosine. Shown below as structure III is an adenosine epoxide having the epoxide substituent at the $N^6$ position. The epoxide can be attached as a cyclopentyl or norbornanyl group.

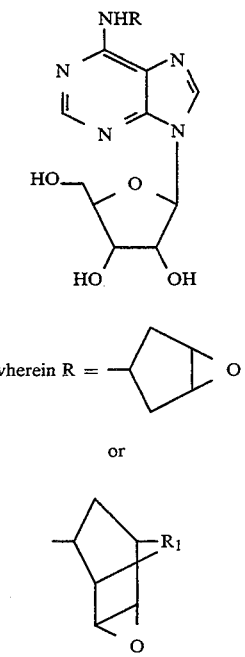

and $R_1$=an alkyl group of 1-4 carbons. The compound can one of four isomers: the 2R-endo, 2R-exo, 2S-endo, or the 2S-exo form.

Figure 2:
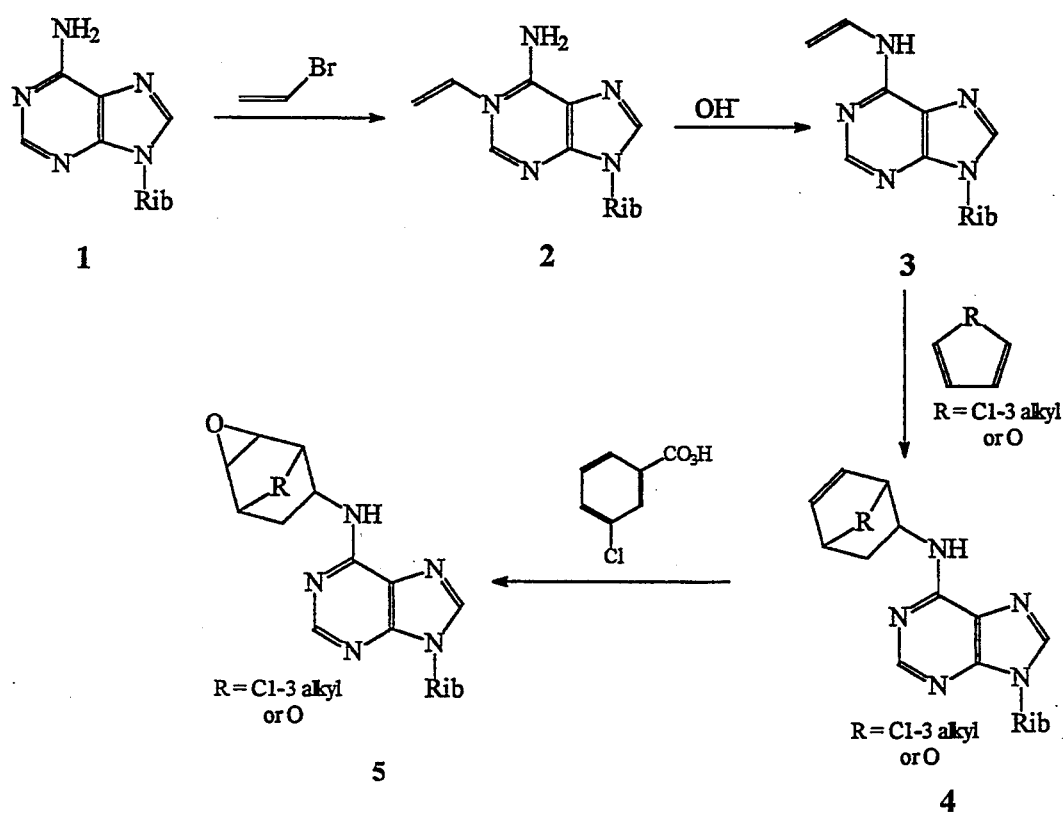
FIG. 2 is a scheme for the synthesis of adenosine derivatives containing an epoxide moiety.

Biological activity can also be enhanced by modifying other parts of the cycloalkyladenosine molecule. For example, both 2- and 5'-chloro substitutions of $N^6$-cycloalkyladenosines can be used to increase $A_1$ selectivity. FIG. 2 shows the steps involved in chemically converting adenosine to a derivative comprising an epoxybicycloalkyl group as an $N^6$ substituent.

The compounds of the subject invention (agonists and antagonists) can be formulated with a pharmaceutically acceptable carrier into a composition that can be administered to a patient who would benefit from the adenosine receptor agonist or antagonist properties of the subject compounds or compositions. Essentially, a patient who has any condition where levels of endogenous adenosine are, or could become, excessive can benefit from therapeutic use of the subject antagonist compound or a composition comprising the compound.

For example, the subject invention pertains to the use of the subject antagonist compounds as diuretics in the treatment of renal failure. In addition, treatments using the subject antagonist compounds or compositions can be employed in the treatment of certain conditions affecting the heart, including bradyarrhythmias associated with hypoxia or ischemia (myocardial infarction), sick sinus node syndrome, and in heart failure, where the positive inotropic effect of the antagonist can be advantageous. The subject antagonists can also be useful as a diuretic or in treatment of renal failure. Other conditions which are recognized as resulting from, or affected by, elevated levels of endogenous adenosine can also be treated with the subject adenosine antagonists.

The subject adenosine agonists can be useful for the treatment of a patient where stimulation of $A_1AR$ is needed. Uses for the subject adenosine agonists and compositions comprising those agonists include their use as a functional β-blocker; as an antiarrhythmic agent for the control of heart rate, including supraventricular tachyarrhythmias, catecholamine (cAMP-dependent) supra- and ventricular-arrhythmias; diabetes type II; and cardioprotection, e.g., decrease infarct size and increase tolerance to myocardial ischemia.

It would be readily recognized in the art that other conditions which can be treated by reducing the effects of elevated endogenous adenosine or by increasing stimulation of the $A_1AR$ can also benefit from the use or administration of the subject adenosine antagonists or agonists, respectively.

Advantageously, dosages of the subject adenosine antagonists for treating post-resuscitation cardiac arrhythmias can be less than the 0.1–20 mg/kg range which has been previously reported for known adenosine antagonists. See U.S. Pat. No. 4,980,379. An effective dose can be recognized as the dose at which the alleviation of bradycardia and reversal of hemodynamic collapse occurs.

Standard procedures for administration of adenosine antagonists such as theophylline and aminophylline at effective dosage levels are well established and are well known to those skilled in the art. For example, the recommended therapeutic range for plasma levels of theophylline for patients with reversible obstruction of the airways is from 10–20 μg/ml. The subject compounds, having high selectivity and potency, can be useful and effective at known concentrations in the blood.

The above list of treatment uses for the subject compounds or compositions is by no means exhaustive, and other situations where the subject invention could be advantageously employed would be readily recognized by ordinarily skilled persons in this art.

Following are examples which illustrate procedures, including the best mode, for practicing the invention. These examples should not be construed as limiting. All percentages are by weight and all solvent mixture proportions are by volume unless otherwise noted.

EXAMPLE 1

Preparation of 8-Epoxyxanthines

Chemistry. The scheme shown in FIG. 1 outlines the syntheses of 1,3-dipropylxanthines having C-8 substituents comprising an epoxide moiety. The reaction of 5,6-diamino-1,3-dipropyluracil, 1, with an ω-alkenoyl halide or an ω-alkenoyl ester gave an amide 2, which was then cyclized in hot alkali to form the 8-ω-alkenyl-1,3-dipropylxanthine 3. Oxidation with m-chloroperbenzoic acid yielded the 8-epoxyalkylxanthine 4. Alternatively, the Dieis-Alder condensation of 3 with a 1,3-cycloalkadiene generated an 8-bicycloalkenylxanthine 5. When furan was the alkadiene the product was the 8-ω-{7-oxabicyclo[2.2.1]hept-2-en-5(6)-yl}xanthine 5a, which contains both (a) an epoxide moiety and (b) an alkenyl moiety that can serve for the formation of a second epoxide moiety. The oxidation of 5a–d with 2.4 equivalents of meta-chloroperbenzoic acid gave the 8-epoxybicycloalkylxanthine 6.

1,3-dipropyl-8-{3-oxatricyclo[3.2.1.0$^{2,4}$]oct-6(7)yl}xanthine. A solution of 8-bicyclo[2.2.1]hept-2-en-5(6)ylxanthine (1.0 g, 3 mmol) and m-chloroperbenzoic acid (0.8 g, 3.6 mmol) in 50 ml $CH_2Cl_2$ was stirred for 24 hours at room temperature. A second aliquot of peracid was added and stirring continued for 24 hours. Evaporation gave a yellow oil that was purified by preparative reverse phase HPLC on C-18 silica eluted with a gradient of 70–80% methanol in water. Yield 0.54 g, 52%, mp 149°–150° C.

1,3-dipropyl-8-{7-oxabicyclo2.2.1]hept-2-en-5(6)yl}xanthine. A suspension of 1,3-dipropyl-8-vinylxanthine (0.4 g, 1.5. mmol) in 50 ml dry THF containing furan (0.22 ml, 3 mmol) was stirred at room temperature. The addition of 1 drop of TMS triflate effected solution, and HPLC showed the disappearance of starting material. Preparative reverse phase HPLC on C-18 silica eluted with a gradient of 50–80% methanol in water yielded 0.25 g (50%) of product.

EXAMPLE 2

Preparation of an Adenosine Derivative Comprising an Epoxide Moiety

A compound useful as an adenosine antagonist is an adenosine derivative comprising a bicycloepoxide bound to the primary amine attached to C-1 or the purine ring. The preparation of the compound is shown in FIG. 2.

EXAMPLE 3

Use of the Novel Compounds as Adenosine Antagonists

In order to demonstrate the effectiveness of the subject compounds as adenosine antagonists, the activity of the compounds was compared to known antagonists. The concentration-response relationship for inhibition of the negative dromotropic effect (S-H prolongation, in milliseconds) of adenosine for the subject compounds, designated ENX and NX, in guinea pig hearts, is shown below in Table 1. The activity for the subject compound is compared to the activities of compounds NAX, CPX, and CPT.

TABLE 1

Comparison of concentrations of various alkylxanthines for inhibition of the negative dromotropic effect of adenosine in guinea pig isolated hearts

| Alkylxanthine | IC$_{50}$ (pM) |
|---|---|
| ENX | 0.01(9) |
| NX | 600 (4) |
| NAX | 1 (5) |
| CPX | 2000 (4) |

TABLE 1-continued

Comparison of concentrations of various alkylxanthines for inhibition of the negative dromotropic effect of adenosine in guinea pig isolated hearts

| Alkylxanthine | IC$_{50}$ (pM) |
|---|---|
| CPT | 9000 (4) |

IC$_{50}$ values are a mean ± SEM of the concentrations of the antagonist required to inhibit 50% of a 16.5 ± 0.06 msec prolongation of stimulus-to-His bundle interval (negative dromotropic effect) induced by adenosine. Numbers in parentheses indicate the number of experiments. Hearts were paced at an atrial interval of 300 msec throughout the experiment. Abbreviations for the alkylxanthines are as follows:
ENX = 1,3-dipropyl-8-{3-oxatricyclo[3.1.2.0$^{2,4}$] oct-6(7)-yl}xanthine;
NX = 1,3-dipropyl-8-(2-norboren-5-yl)xanthine;
NAX = 1,3-dipropyl-8-(3-noradamantyl)xanthine;
CPX = 8-cyclopentyl-1,3-dipropylxanthine; and
CPT = 8-cyclopentyl-1,3-dimethylxanthine.

The binding affinities for the adenosine receptor of ENX are described in Table 2.

TABLE 2

Binding affinities of alkylxanthines for the A$_1$—and A$_2$—adenosine receptors in brain, DDT$_1$—MF$_2$ and PC-12 cell membranes

| Alkyl- | K$_i$ (nM) | | |
|---|---|---|---|
| xanthine | Brain | DDT$_1$MF$_2$ | PC-12 |
| ENX | 4.0 ± 0.6 (5) | 0.22 ± 0.03 (5) | 11,666 ± 366 (4) |
| CPX | 4.4 ± 0.8 (4) | 0.13 ± 0.01 (4) | 320 ± 40 (3) |
| NAX | 3.8 ± 0.21 (4) | 0.18 ± 0.05 (3) | — |
| CPT | 41.0 ± 13.0 (4) | — | — |

A$_1$ receptor binding was carried out with [$^3$H] CPX in guinea pig forebrain and cardiac membranes, and in intact DDT$_1$—MF$_2$ cells. A$_2$ receptor binding was carried out with [$^3$H] NECA in PC-12 cell membranes. Values are mean ± SEM of triplicate determinations in each of several (n) preparations. K$_i$ values were calculated as described in methods. Abbreviations for the alkylxathines are as follows:
ENX = 1,3-dipropyl-8-{3-oxatricyclo[3.1.2.0$^{2,4}$] oct-6(7)-yl}xanthine;
CPX = 8-cyclopentyl-1,3-dipropylxathine;
NAX = 1,3-dipropyl-8-(3-noradamantyl)xanthine; and
CPT = 8-cyclopentyl-1,3-dimethylxanthine.

EXAMPLE 4

Synthesis of N$^6$-Substituted Adenosine Derivatives

The subject agonist compounds shown as Structure IV can be synthesized according to known procedures. For example, the general synthesis scheme for obtaining these compounds initially involves alkylation of an appropriately substituted amine, e.g., a bicyclic amine, with 6-chloropurine riboside. This straightforward reaction has been commonly used for the synthesis of N$^6$-substituted adenosines. See WO 84 04 882 (1985).

The substituted amine can be functionalized with a double bond which can then be oxidized to generate the epoxide product. m-Chloroperbenzoic acid can be used for this oxidation reaction. See also Sharpless, K. B., W. Amberg, Y. L. Bennani, G. A. Crispino, J. Hartung, K.-S. Jeong, H.-L. Kwong, K. Morikawa, Z.-M. Wong, D. Xu, X.-L. Zhang (1992) *J. Org. Chem.* 57:2768–2771; and Kolb, H. C., B. K. Sharpless (1992) *Tetrahedron* 48:1015–1030.

An alternative method of generating epoxides is the osmium-catalyzed dihydroxylation of olefins, which is now well known in view of the discovery of phthalazine ligands and that osmate ester hydrolysis is acceleration by organic sulfomamides. A simple, one-pot procedure for the conversion of vicinal diols into epoxides is known in the art (Kolb, H. C., B. K. Sharpless, supra). This reaction proceeds without epimerization via halohydrin ester intermediates. Combination of these methods allows epoxides to be obtained from olefins in a stereospecific fashion.

The substituted amines which can be used for synthesis of the subject compounds shown as Structure 1V are 3-cyclopenten-1-yl amine (for the cyclopentene oxide derivative of adenosine) or 5-norbornen-2-yl amine (for the cyclohexene epoxide derivative of adenosine). 3-Cyclopenten-1-yl-amine can be synthesized from cis-1,4-dichlorobutene and diethyl malonate via a 5-step reaction sequence which is known in the art (Murdock, K. C., R. B. Angier [1962] *J. Org. Chem.* 27:2395–2398).

The synthesis of 5-norbornene-2-yl amine proceeds from 5-norbornene-2-carboxylic acid, commercially available as a mixture of four isomers, 2R and 2S, each endo and exo. Conversion of this carboxylic acid to acyl chloride, followed by treatment with sodium azide, yields an acyl azide. Curtius rearrangement (loss of N$_2$ and migration of the substituent group) and subsequent hydrolysis yields 5-norbornen-2-yl amine as a mixture of isomers. This reaction sequence can be performed as a continuous operation without the isolation of the acyl azide or isocyanate in the synthesis of 4-aminocyclohexene. Another variation used for the Curtius rearrangement involves the preparation of the acyl azide by treatment of the corresponding acyl hydrazine with nitrous acid. In both cases, the configuration of the substituent group is retained. The endo and exo components can be separated by HPLC methods known in the art.

Figure 3:
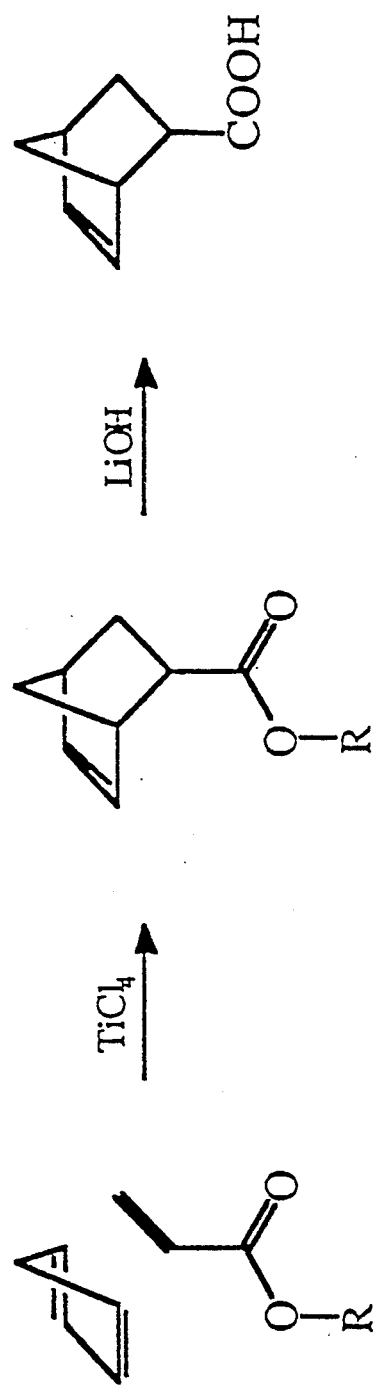
FIG. 3 shows synthesis of (2S)- and (2S)-endo-5-norbornen-2-carboxylic acids.
Figure 3:
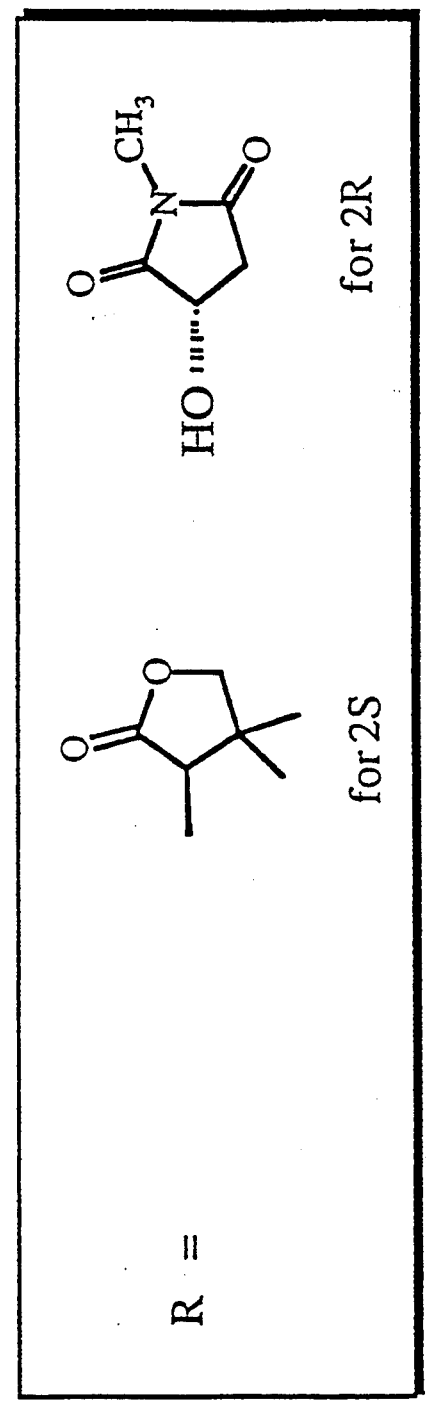

The synthesis of the diastereomerically pure 5-norbornen-2-yl amines involves the use of asymmetric Dieis-Alder reactions to obtain intermediate carboxylic acids, followed by a Curtius rearrangement as described above. A general scheme for synthesizing these compounds is shown in FIG. 3.

EXAMPLE 5

Uses, Formulations, and Administrations

Therapeutic and prophylactic application of the subject compounds, and compositions comprising them, can be accomplished by any suitable method and technique presently or prospectively known to those skilled in the art. Further, the compounds of the invention have use as starting materials or intermediates for the preparation of other useful compounds and compositions. The compounds of the invention are useful for various non-therapeutic and therapeutic purposes. It is apparent from the testing that the compounds of the invention have effective antiarrhythmic activity. Specifically, they are useful in regulating cardiac arrhythmia, including PVST, in animals and humans.

The demonstrated effects of both the agonists and the antagonists on cardiac chronotropy, dromotropy, and inotropy make them useful therapeutically as either stimulants or modulators of cardiac performance, thereby affecting function of the heart. For example, the regulation or modulation activity of the subject compounds can affect heart rate (chronotropic effect) and impulse conduction (dromotropic effect). The subject compounds can also be used diagnostically to determine parameters of cardiac function, e.g., as pharmacological reagents useful in determining whether adenosine receptors are mediators of dysfunction of the heart or other organs.

The subject compounds can also serve as standards for in vitro and in vivo studies that measure or compare activities of other agonists and antagonists that act directly or indirectly through adenosine receptors. As reagents for such comparisons, the compounds are valuable pharmacological tools. Their high affinity and selectivity for the A$_1$ adenosine receptor make them important sources of information about the function of those receptors throughout the body.

Other uses for the subject compounds include their use in the characterization of structure or location of adenosine receptors in organs or tissues. This can be done by, for example, attaching an appropriate label or reporter to the subject compounds by standard techniques or procedures known to persons of ordinary skill in the art. The labels that are suitable for conjugation to the compounds of the subject invention include, but are not limited to, radiolabels (e.g., radioisotopes), fluorescent labels, and biotin labels. Radioisotopes that are suitable for labeling the subject compounds include Bromine-77, Fluorine-18, Iodine-131, Iodine-123, Iodine-125, Iodine-126, Iodine-133, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Technetium-99m, Tellurium-121m, Tellurium-99m, Tellurium-125m, Thulium-165, Thulium-167, Thulium-168, and Tritium. The gamma-emitting Indium species and Technetium-99m are preferred isotopes because these isotopes are detectable with a gamma-camera and have favorable half lives for imaging in vivo..Alternatively, it would be recognized by those of ordinary skill in the art that non-radioactive labels, for example, enzyme-substrate complexes, e.g., biotin-avidin, horseradish peroxidase-alkaline phosphatase, and the like could be used. Also, fluorescent entities suitable for labeling the subject compounds include fluorescein sodium, fluorescein isothiocyanate, and Texas red sulfonyl chloride. As such, the compounds can be used to visualize, in vitro or in vivo, structure or function of organs or tissues in which the $A_1$ adenosine receptors are present.

A further embodiment of the subject invention involves the use of the compounds to direct therapeutic compounds to the $A_1$ adenosine receptor site. Because of the specificity of the compounds of the subject invention, they can be conjugated to therapeutic compounds in order to direct the therapeutic compound to the vicinity of $A_1$ adenosine receptor. Also, in the case of compounds of the subject inventions which have selectivity to a specific type of tissue, such as heart tissue, these compounds can be used to direct therapeutic or diagnostic reagents to those locations.

The administration of the subject compounds of the invention is useful as an antiarrhythmic agent. Thus, pharmaceutical compositions containing compounds of the invention as active ingredients are useful in prophylactic or therapeutic treatment of cardiac arrhythmias in humans or other mammals.

The dosage administered will be dependent upon the antiarrhythmic response desired; the type of host involved; its age, health, weight, kind of concurrent treatment, if any; frequency of treatment; therapeutic ratio and like considerations. Advantageously, dosage levels of the administered active ingredients can be, for examples, dermal, 1 to about 500 mg/kg; orally, 0.01 to 200 mg/kg; intranasal 0.01 to about 100 mg/kg; and aerosol 0.01 to about 50 mg/kg of animal body weight.

Expressed in terms of concentration, the active ingredient of the invention can be present in the new compositions for use dermally, intranasally, bronchially, intramuscularly, intravaginally, intravenously, or orally in a concentration of from about 0.01 to about 50% w/w of the composition, and especially from about 0.1 to about 30% w/w of the composition.. Preferably, the novel compound is present in a composition from about 1 to about 10% and, most preferably, the novel composition comprises about 5% novel compound.

The compositions of the invention are advantageously used in a variety of forms, e.g., tablets, ointments, capsules, pills, powders, aerosols, granules, and oral solutions or suspensions and the like containing the indicated suitable quantities of the active ingredient. Such compositions are referred to herein and in the accompanying claims generically as "pharmaceutical compositions." Typically, they can be in unit dosage form, namely, in physically discrete units suitable as unitary dosages for human or animal subjects, each unit containing a predetermined quantity of active ingredient calculated to produce the desired therapeutic or prophylactic effect in association with one or more pharmaceutically acceptable other ingredients, e.g., diluent or carrier.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

Where the pharmaceutical compositions are ointments, the active ingredient can be mixed with a diluent vehicle such as cocoa butter, viscous polyethylene glycols, hydrogenated oils, and such mixtures can be emulsified if desired.

In accordance with the invention, pharmaceutical compositions comprise, as an active ingredient, an effective amount of one or more non-toxic, pharmaceutically acceptable ingredient(s). Examples of such ingredients for use in the compositions include ethanol, dimethyl sulfoxide, glycerol, silica, alumina, starch, calcium carbonate, talc, flour, and equivalent non-toxic carriers and diluents.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound having the formula

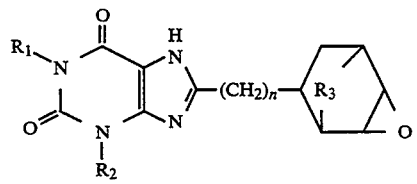

wherein $R_1=R_2=$n-propyl, $R_3=CH_2$, and $n=0$.

2. A diuretic pharmaceutical composition comprising a compound having the chemical formula

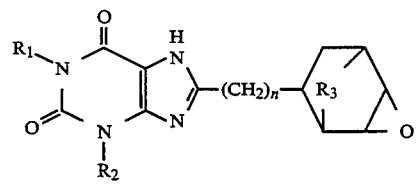

wherein $R_1=R_2=$n-propyl, $R_3=CH_2$, and $n=0$; and a pharmaceutically acceptable carrier.

3. A method for producing diuresis in a patient, said method comprising administering to said patient an effective amount of a compound having the formula
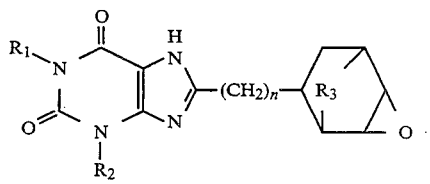
wherein $R_1=R_2=$n-propyl, $R_3=CH_2$, and $n=0$.
* * * * *

UNITED STATES PATENT AND TRADEMARK OFFICE
CERTIFICATE OF CORRECTION

PATENT NO. : 5,446,046
DATED : August 29, 1995
INVENTOR(S) : Luiz Belardinelli, et. al.

It is certified that error appears in the above-indentified patent and that said Letters Patent is hereby corrected as shown below:

Column 6: line 3: "Dieis-Alder" should read --Diels-Alder--; line 24: "oxabicyclo 2.2.1]" should read --oxabicyclo[2.2.1]--.

Column 7: line 12: "(2-norboren-5-yl)" should read --(2-norbornen-5-yl)--; line 32: "dipropylxathine" should read --dipropylxanthine--; line 34: "dimethylxathine" should read --dimethylxanthine--; line 44: "used :for" should read --used for--; line 67: "1V" should read --IV--.

Column 8: line 26: "Dieis-Alder" should read --Diels-Alder--; line 52: "or :modulation" should read --or modulation--.

Column 9: line 67: "composition.." should read --composition.--.

Column 10: line 54: "n-propyl," should read --n-propyl,--.

Signed and Sealed this

Second Day of January, 1996

Attest:

BRUCE LEHMAN

Attesting Officer

Commissioner of Patents and Trademarks